United States Patent
Chen et al.

(10) Patent No.: US 10,088,113 B1
(45) Date of Patent: Oct. 2, 2018

(54) ILLUMINATION APPARATUS

(71) Applicant: Industrial Technology Research Institute, Hsinchu (TW)

(72) Inventors: Kuang-Vu Chen, Taipei (TW); Yen-Chang Wang, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/856,056

(22) Filed: Dec. 28, 2017

(30) Foreign Application Priority Data

Dec. 26, 2017 (TW) .............................. 106145722 A (51) Int. Cl.
*F21K 9/68* (2016.01)
*F21K 9/62* (2016.01)
*F21K 9/275* (2016.01)
*F21K 9/272* (2016.01)
*A61B 1/06* (2006.01)
*A61B 1/07* (2006.01)

(52) U.S. Cl.
CPC .............. *F21K 9/275* (2016.08); *F21K 9/272* (2016.08); *F21K 9/62* (2016.08); *F21K 9/68* (2016.08); *A61B 1/0684* (2013.01); *A61B 1/07* (2013.01); *F21V 2200/17* (2015.01)

(58) Field of Classification Search
CPC ..... A61B 1/06–1/07; F21V 2200/00–2200/40; G02B 6/0096; F21K 9/61; F21K 9/68; F21K 9/62
See application file for complete search history.

(56) References Cited

U.S. PATENT DOCUMENTS 4,459,642 A * 7/1984 Mori ..................... F21S 11/00
359/595
4,895,138 A 1/1990 Yabe
(Continued)

FOREIGN PATENT DOCUMENTS

CN 102209926 10/2011
CN 202812907 3/2013
(Continued)

OTHER PUBLICATIONS

"Office Action of Taiwan Counterpart Application," dated Feb. 22, 2018, p. 1-p. 3, in which the listed references were cited.
(Continued)

*Primary Examiner* — Mariceli Santiago
(74) *Attorney, Agent, or Firm* — JCIPRNET (57) ABSTRACT

An illumination apparatus includes an outer tube, an inner tube, and a light source. The outer tube has a reflecting inner wall. The inner tube is disposed in the outer tube and coaxial with the outer tube. The inner tube has a reflecting outer wall. A ring-shaped light channel is formed between the outer tube and the inner tube. The ring-shaped light channel has a light entrance and a light exit corresponding to two ends of the outer tube respectively. A segment of the inner tube protrudes from the light exit. The light source is disposed at the light entrance. A light beam emitted from the light source enters the ring-shaped light channel through the light entrance, is reflected multiple times by the reflecting inner wall of the outer tube and the reflecting outer wall of the inner tube, and travels out of the illumination apparatus through the light exit.

22 Claims, 8 Drawing Sheets

(56) References Cited

U.S. PATENT DOCUMENTS

| | | | |
|---|---|---|---|
| 6,449,006 B1 | 9/2002 | Shipp | |
| 7,611,271 B2 | 11/2009 | Meis et al. | |
| 7,699,490 B2 * | 4/2010 | Tsai | F21S 6/004 |
| | | | 362/101 |
| 7,918,791 B2 | 4/2011 | Lu et al. | |
| 8,308,637 B2 | 11/2012 | Ishigami et al. | |
| 8,400,500 B2 | 3/2013 | Hirata | |
| 8,410,414 B2 | 4/2013 | Wu et al. | |
| 8,430,513 B2 | 4/2013 | Chang et al. | |
| 8,449,457 B2 | 5/2013 | Aizenfeld et al. | |
| 8,451,368 B2 | 5/2013 | Sung et al. | |
| 8,467,578 B2 | 6/2013 | Chang et al. | |
| 8,480,566 B2 | 7/2013 | Farr | |
| 8,636,653 B2 | 1/2014 | Wilson | |
| 8,822,902 B2 | 9/2014 | Lyu et al. | |
| 8,873,034 B2 | 10/2014 | Lin et al. | |
| 8,894,206 B2 | 11/2014 | Lee et al. | |
| 8,928,746 B1 | 1/2015 | Stevrin et al. | |
| 8,988,518 B2 | 3/2015 | Cheng et al. | |
| 9,116,101 B2 | 8/2015 | Chen et al. | |
| 2002/0143239 A1 * | 10/2002 | Henzler | A61B 1/0676 |
| | | | 600/179 |
| 2006/0069313 A1 * | 3/2006 | Couvillon, Jr. | A61B 5/06 |
| | | | 600/179 |
| 2011/0291560 A1 * | 12/2011 | Wang | F21V 29/83 |
| | | | 315/32 |
| 2012/0041290 A1 | 2/2012 | Perelman | |
| 2012/0249765 A1 | 10/2012 | Cheng et al. | |
| 2013/0281858 A1 | 10/2013 | Huang et al. | |
| 2015/0105617 A1 | 4/2015 | Wilson | |
| 2015/0293222 A1 | 10/2015 | Huang et al. | |
| 2016/0044216 A1 | 2/2016 | Chang et al. | |
| 2017/0215714 A1 | 8/2017 | Shinji et al. | |
| 2017/0265734 A1 * | 9/2017 | Vayser | A61B 1/07 |

FOREIGN PATENT DOCUMENTS

| | | | | |
|---|---|---|---|---|
| CN | 103987307 | | 8/2014 | |
| CN | 206391328 | | 8/2017 | |
| EP | 0520743 A1 | * | 12/1992 | A61B 1/00142 |
| JP | 2016202192 A | * | 12/2016 | A61B 1/00165 |
| TW | 201407101 | | 2/2014 | |
| TW | 201504577 | | 2/2015 | |
| TW | M497797 | | 3/2015 | |
| TW | I517830 | | 1/2016 | |
| TW | I571227 | | 2/2017 | |

OTHER PUBLICATIONS

Jing Chen, et al., "Reconstruction and Processing of Medical Electronic Endoscopic Image Based on White LED Illumination," Proc. of SPIE vol. 8200, Nov. 29, 2011, pp. 820008-1-820008-7.

Wei-De Jeng, et al., "Design of illumination system in ring field capsule endoscope," Proc. of SPIE vol. 7893, Feb. 2011, pp. 78930E-1-78930E-9.

Ming-Kuan Lu, et al., "Compact light-emitting diode lighting ring for video-assisted thoracic surgery," Journal of Biomedical Optics, vol. 19, No. 10, Oct. 2014, pp. 105004-1-105004-4.

Alex C. H. Lee, et al., "Solid-state semiconductors are better alternatives to arc-lamps for efficient and uniform Ilumination in minimal access surgery," Surg Endosc., vol. 23, No. 3, Mar. 2009, pp. 1-9.

Jing-Tao Dong, et al., "Optical design of color light-emitting diode ring light for machine vision inspection," Optical Engineering, vol. 50, No. 4, Apr. 2011, pp. 043001-1-043001-11.

Ivan Moreno, et al., "Designing light-emitting diode arrays for uniform near-field irradiance," Applied Optics, vol. 45, No. 10, Apr. 1, 2006, pp. 2265-2272.

Mang Ou-Yang, et al., "Improving the uniformity of luminous system in radial imaging capsule endoscope system," Optical Engineering, vol. 52, No. 2, Feb. 2013, pp. 023003-1-023003-1-11.

Antonio Di Ieva, et al., "A Journey into the Technical Evolution of Neuroendoscopy," World Neurosurgery, vol. 82, No. 6, Dec. 2014, pp. e777-e789.

Gabriel Zada, et al., ""Through the Looking Glass": Optical Physics, Issues, and the Evolution of Neuroendoscopy," World Neurosurgery, vol. 77, No. 1, Jan. 2012, pp. 92-102.

Yoko Kato, et al., "Neuroendoscope in Aneurysm Surgeries: Past, Present and Future," J Bras Neurocirurg, vol. 19, No. 2, 2008, pp. 36-41.

Francis Nguyen, et al., "Realizing LED illumination lighting applications," Proc. of SPIE vol. 5941, Sep. 2, 2005, pp. 594105-1-594105-6.

Wikipedia, "Wikipedia: Capsule endoscopy", Retrieved on Jan. 2018, Available at: https://en.wikipedia.org/wiki/Capsule_endoscopy.

V. B. S. Prasath, "Illumination Estimation in Capsule Endoscopy Images," Retrieved on Jan. 2018, Available at: https://sites.google.com/site/suryaiit/research/endoscopy/illumination.

\* cited by examiner

ILLUMINATION APPARATUS

CROSS-REFERENCE TO RELATED APPLICATION

This application claims the priority benefit of Taiwan application serial no. 106145722, filed on Dec. 26, 2017. The entirety of the above-mentioned patent application is hereby incorporated by reference herein and made a part of this specification.

BACKGROUND

Technical Field

The disclosure relates to an illumination apparatus.

Description of Related Art

Generally, in terms of use for illumination, a more uniform luminance of an illumination region helps the user to observe the illumination region. However, the illumination range of a common illumination apparatus (e.g., an endoscope illumination apparatus) is mainly concentrated on the region right in front of the illumination apparatus. As a result, the luminance is overly high in the frontal region but drops quickly in a region that is at a larger viewing angle and away from the frontal region, which causes the illumination region to have poor luminance uniformity and affects the user's observation of the illumination region.

SUMMARY

According to an embodiment of the disclosure, an illumination apparatus including an outer tube, an inner tube, and a light source is provided. The outer tube has a reflecting inner wall. The inner tube is disposed in the outer tube and is coaxial with the outer tube. The inner tube has a reflecting outer wall. A ring-shaped light channel is formed between the outer tube and the inner tube. The ring-shaped light channel has a light entrance and a light exit corresponding to two ends of the outer tube respectively, and a segment of the inner tube protrudes from the light exit. The light source is disposed at the light entrance. A light beam emitted from the light source enters the ring-shaped light channel through the light entrance, is reflected multiple times by the reflecting inner wall of the outer tube and the reflecting outer wall of the inner tube, and then travels out of the illumination apparatus through the light exit.

Several exemplary embodiments accompanied with figures are described in detail below to further describe the disclosure in detail.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DETAILED DESCRIPTION OF DISCLOSED EMBODIMENTS

Figure 1A:
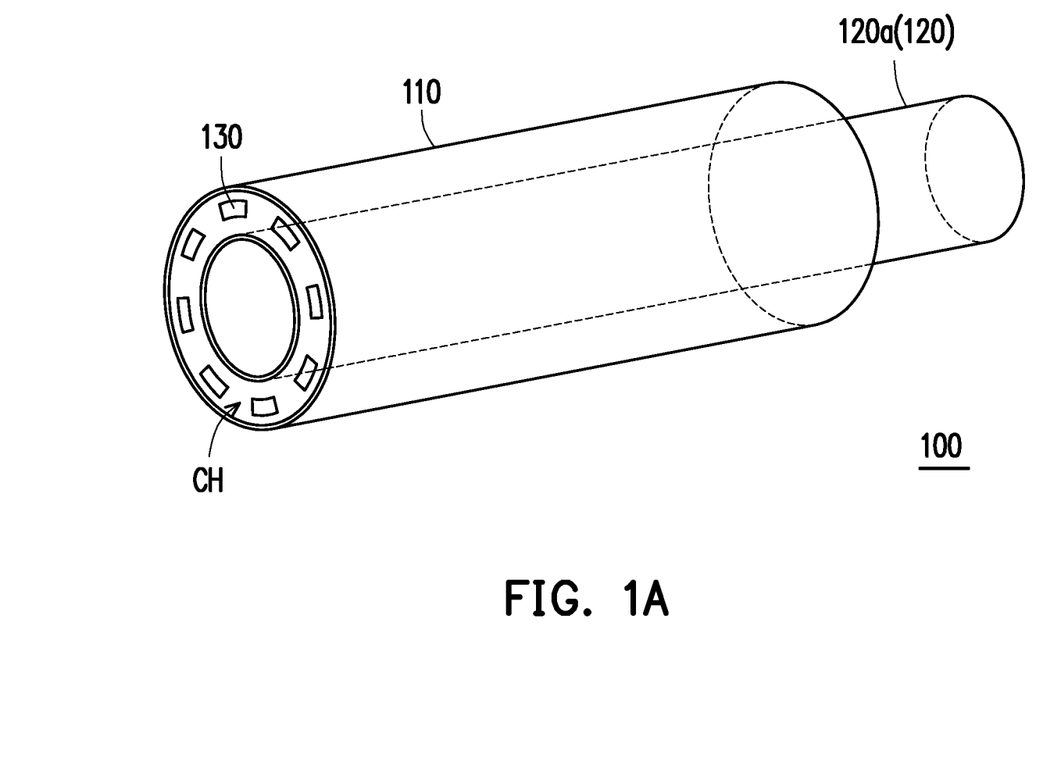
FIG. 1A is a schematic view of the illumination apparatus according to an embodiment of the disclosure.
Figure 1B:
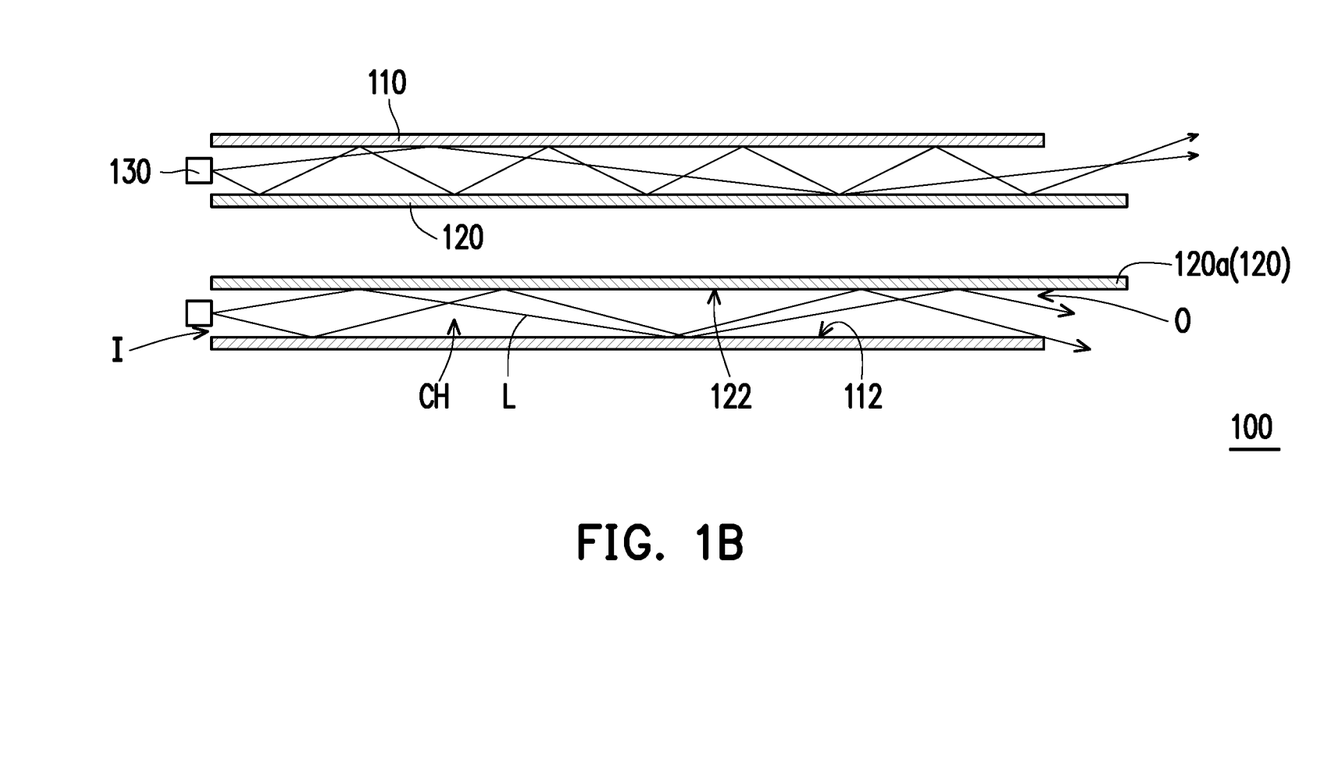
FIG. 1B is a schematic cross-sectional view of the illumination apparatus along the central axis according to an embodiment of the disclosure.

FIG. 1A is a schematic view of an illumination apparatus according to an embodiment of the disclosure. FIG. 1B is a schematic cross-sectional view of the illumination apparatus along a central axis according to an embodiment of the disclosure. Referring to FIG. 1A and FIG. 1B, the illumination apparatus 100 of this embodiment includes an outer tube 110, an inner tube 120, and a light source 130. The outer tube 110 has a reflecting inner wall 112. The inner tube 120 is disposed in the outer tube 110 and is coaxial with the outer tube 110, wherein the inner tube 120 has a reflecting outer wall 122. A ring-shaped light channel CH is formed between the outer tube 110 and the inner tube 120. Moreover, the ring-shaped light channel CH has a light entrance I and a light exit O corresponding to two ends of the outer tube 110 respectively, and a segment 120a of the inner tube 120 protrudes from the light exit O. The light source 130 is disposed at the light entrance I, and a light beam L emitted from the light source 130 enters the ring-shaped light channel CH through the light entrance I, is reflected multiple times by the reflecting inner wall 112 of the outer tube 110 and the reflecting outer wall 122 of the inner tube 120, and then travels out of the illumination apparatus 100 through the light exit O. In this embodiment, since the segment 120a of the inner tube 120 protrudes from the light exit O, more light beams L are emitted out of the illumination apparatus 100 in a direction away from the inner tube 120. Therefore, the light beam L has a larger divergence angle when traveling out of the illumination apparatus 100, such that the luminance of a region at a larger viewing angle is improved and the light beam L is not overly concentrated on the region right in front of the illumination apparatus 100. As a result, the illumination apparatus 100 of the embodiment of the disclosure has a uniform luminance.

In this embodiment, the light source 130 is a plurality of discontinuous point-type light-emitting elements, which is, for example, composed of a plurality of light-emitting diodes (LEDs). In other embodiments (not shown here), the light source may be a continuous surface-type light-emitting element, which is composed of an organic light-emitting diode (OLED), for example. In addition, the light source 130 may include a light-guiding optical fiber bundle or a light guide connected to the light entrance I of the ring-shaped light channel CH. In other words, the light-emitting element may not be disposed directly at the light entrance I of the ring-shaped light channel CH. Instead, the light emitted from the light-emitting element is guided by the light-guiding optical fiber bundle or the light guide to the light entrance I of the ring-shaped light channel CH. Nevertheless, the disclosure is not limited thereto.

In this embodiment, a material of the outer tube 110 and the inner tube 120 is a metal, for example, and the reflecting inner wall 112 of the outer tube 110 and the reflecting outer wall 122 of the inner tube 120 have smooth surfaces, for example, such that the reflection type of the light beam L between the reflecting inner wall 112 of the outer tube 110 and the reflecting outer wall 122 of the inner tube 120 is specular reflection. In other embodiments, the reflecting inner wall 112 of the outer tube 110 and the reflecting outer wall 122 of the inner tube 120 have rough surfaces, for example, such that the reflection type of the light beam L between the reflecting inner wall 112 of the outer tube 110 and the reflecting outer wall 122 of the inner tube 120 is diffuse reflection.

Figure 2:
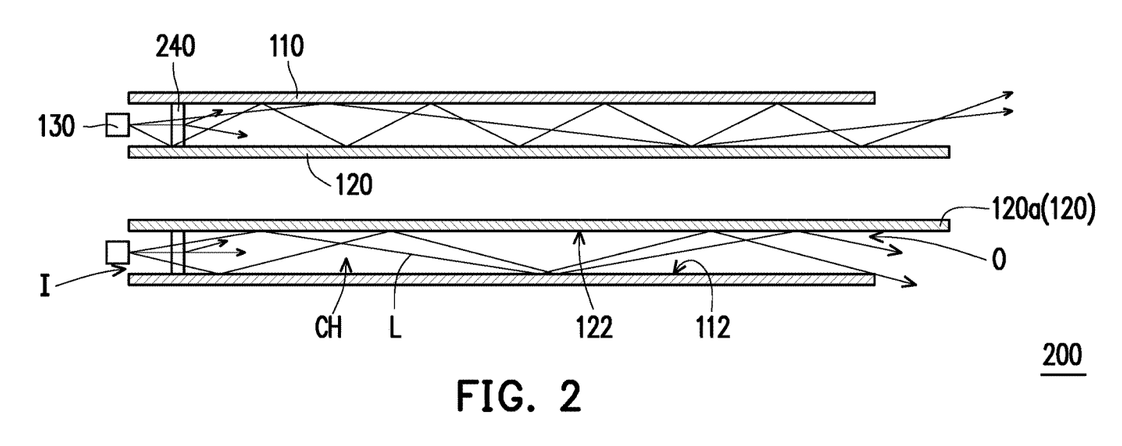
FIG. 2 is a schematic cross-sectional view of the illumination apparatus along the central axis according to an embodiment of the disclosure.

FIG. 2 is a schematic cross-sectional view of the illumination apparatus along the central axis according to an embodiment of the disclosure. Referring to FIG. 2, the illumination apparatus 200 of this embodiment is substantially the same as the illumination apparatus 100 shown in FIG. 1B. It should be noted that the illumination apparatus 200 further includes a light diffusion structure 240 disposed in the ring-shaped light channel CH, and the light diffusion structure 240 has an ring shape corresponding to the ring-shaped light channel CH. Specifically, the light diffusion structure 240 is capable of diverging the light that passes through, such that the light beam L emitted from the light source 130 is further dispersed and becomes uniform after passing through the light diffusion structure 240. For example, the light diffusion structure 240 may be a transparent material and have a rough surface. The light diffusion structure 240 may also include a scattering material dispersed in the light diffusion structure 240. In addition, the light diffusion structure 240 may also include a holographic diffuser. Nevertheless, the disclosure is not limited thereto.

Figure 3:
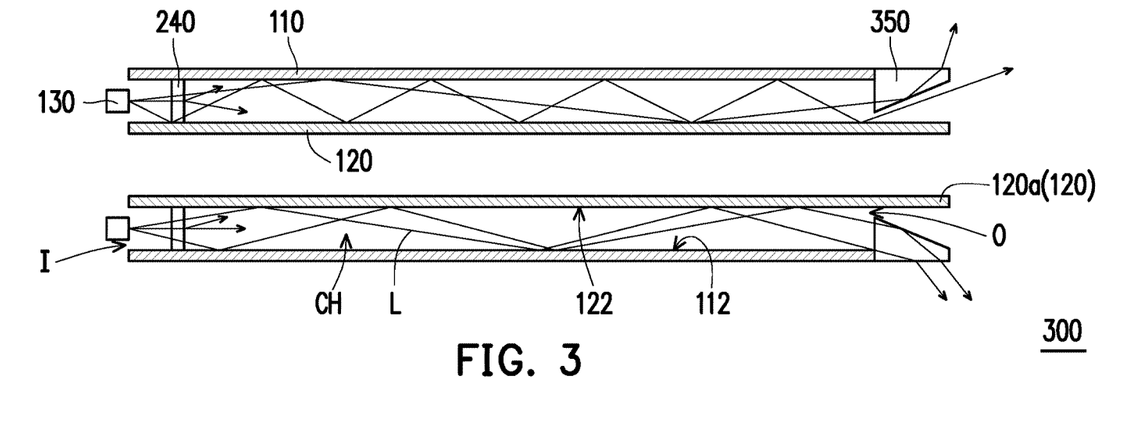
FIG. 3 is a schematic cross-sectional view of the illumination apparatus along the central axis according to an embodiment of the disclosure.
Figure 6:
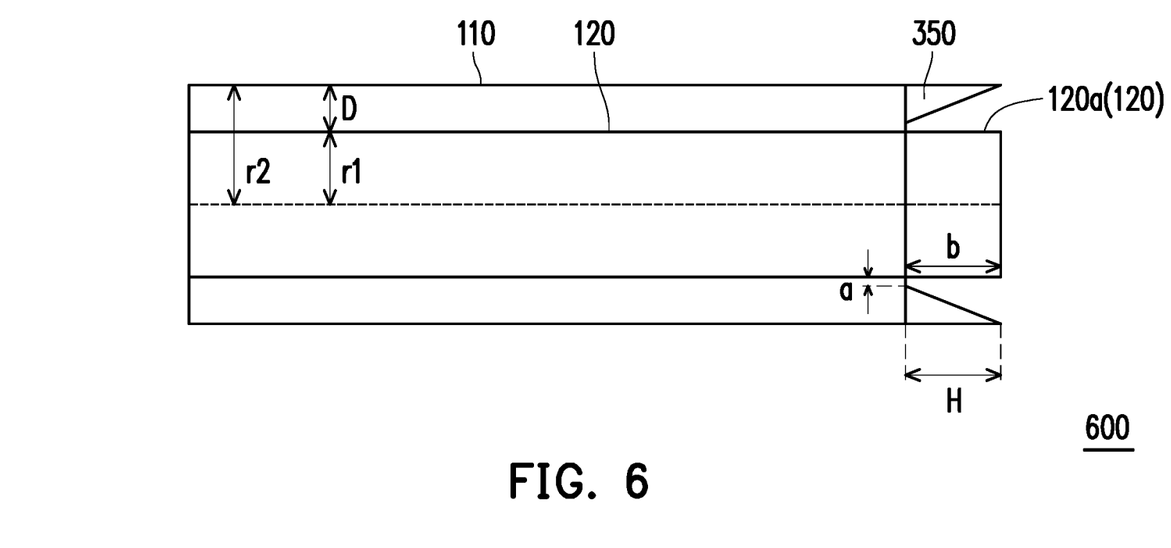
FIG. 6 is a schematic diagram of the design of the illumination apparatus according to an embodiment of the disclosure.

FIG. 3 is a schematic cross-sectional view of the illumination apparatus along the central axis according to an embodiment of the disclosure. Referring to FIG. 3, the illumination apparatus 300 of this embodiment is substantially the same as the illumination apparatus 200 shown in FIG. 2. It should be noted that the illumination apparatus 300 further includes a refractive structure 350 disposed at the light exit O of the ring-shaped light channel CH and connected to the outer tube 110. The refractive structure 350 is a ring-shaped structure. An outer diameter of the refractive structure 350 is equal to an outer diameter of the outer tube 110, and an inner diameter of the refractive structure 350 at a junction with the outer tube 110 is smaller than an inner diameter of the refractive structure 350 at an end away from the outer tube 110. Additionally, the inner diameter of the refractive structure 350 at the junction with the outer tube 110 is greater than an outer diameter of the inner tube 120. In other words, a distance exists between the refractive structure 350 and the inner tube 120 at the light exit O. Moreover, the inner diameter of the refractive structure 350 at the end away from the outer tube 110 is smaller than or equal to the outer diameter of the outer tube 110. It should be understood that the inner diameter mentioned here refers to a radius from the inner surface of the component to the central axis of the illumination apparatus 300, and the outer diameter refers to a radius from the outer surface of the component to the central axis of the illumination apparatus 300. In this embodiment, the inner diameter of the refractive structure 350 at the end away from the outer tube 110 is smaller than the outer diameter of the outer tube 110. Therefore, a cross-sectional shape of the refractive structure 350 is a trapezoidal shape. In other embodiments (as shown in FIG. 6, for example), the inner diameter of the refractive structure 350 at the end away from the outer tube 110 may be equal to the outer diameter of the outer tube 110, and therefore the cross-sectional shape of the refractive structure 350 may also be a triangular shape. Nevertheless, the disclosure is not limited thereto.

In this embodiment, the refractive structure 350 is a transparent material. After being reflected multiple times by the reflecting inner wall 112 of the outer tube 110 and the reflecting outer wall 122 of the inner tube 120, the light beam L emitted from the light source 130 is refracted by the refractive structure 350 or totally internally reflected in the refractive structure 350, so as to travel out of the illumination apparatus 300 in a direction further away from the inner tube 120. A material of the refractive structure 350 is glass, plastic, acrylic, or other suitable transparent material, for example. Since the refractive structure 350 further refracts the light beam L outward to travel out of the illumination apparatus 300, the light beam L has a larger divergence angle when traveling out of the illumination apparatus 300. Therefore, the illumination apparatus 300 has a uniform luminance. In addition, the refractive structure 350 is connected to the outer tube 110 and has the same outer diameter as the outer tube 110. In other words, the illumination apparatus 300 has a continuous and intact outer contour without a step height difference between the outer tube 110 and the inner tube 120 at one end of the light exit O, so as to be suitable for endoscopy illumination. However, in other embodiments (not shown here), the outer diameter of the refractive structure 350 may be different from the outer diameter of the outer tube 110.

In this embodiment, the illumination apparatus 300 is provided with both the refractive structure 350 and the light diffusion structure 240. However, in other embodiments (not shown here), the illumination apparatus may include only the refractive structure 350 without the light diffusion structure 240.

Figure 4:
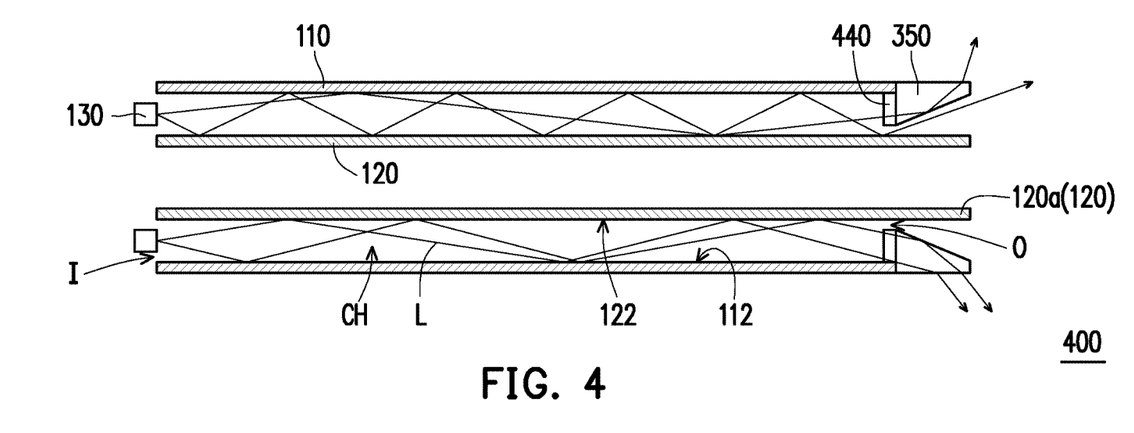
FIG. 4 is a schematic cross-sectional view of the illumination apparatus along the central axis according to an embodiment of the disclosure.

FIG. 4 is a schematic cross-sectional view of the illumination apparatus along the central axis according to an embodiment of the disclosure. Referring to FIG. 4, the illumination apparatus 400 of this embodiment is substantially the same as the illumination apparatus 300 shown in FIG. 3, but it should be noted that the light diffusion structure 240 of the illumination apparatus 300 is disposed in the ring-shaped light channel CH at a location closer to the light entrance I, while a light diffusion structure 440 of the illumination apparatus 400 is disposed on the refractive structure 350 and close to the light exit O of the ring-shaped light channel CH. In an embodiment, the light diffusion structure 440 and the refractive structure 350 are integrally formed.

Figure 5:
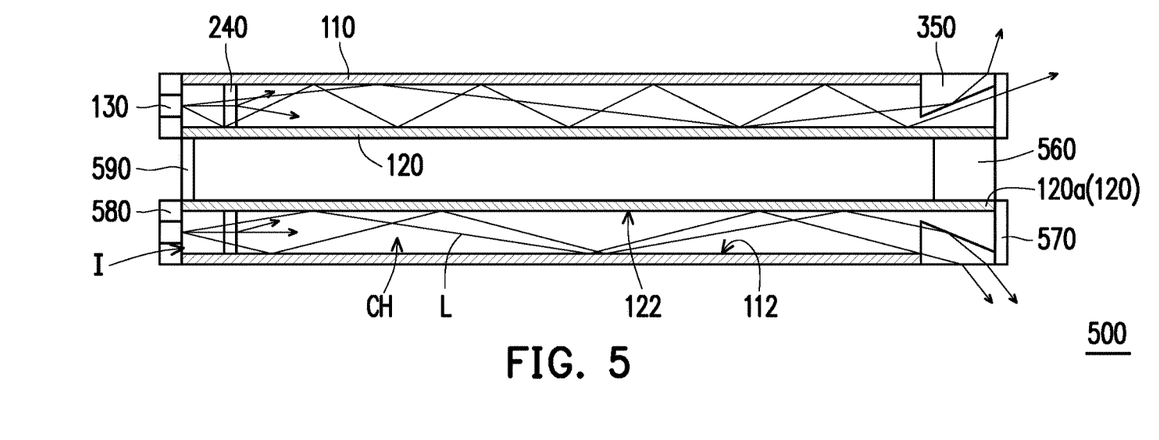
FIG. 5 is a schematic cross-sectional view of the illumination apparatus along the central axis according to an embodiment of the disclosure.

FIG. 5 is a schematic cross-sectional view of the illumination apparatus along the central axis according to an embodiment of the disclosure. Referring to FIG. 5, the illumination apparatus 500 of this embodiment is substantially the same as the illumination apparatus 300 shown in FIG. 3. It should be noted that the illumination apparatus 500 further includes an image capturing device 560 disposed in the inner tube 120 at an end close to the segment 120a. In addition, the illumination apparatus 500 further includes a sealing structure 570, a sealing structure 580, and a sealing structure 590. The sealing structure 570 seals a gap between the refractive structure 350 and the inner tube 120. The sealing structure 580 seals a gap between the light source 130 and the light entrance I of the ring-shaped light channel CH. The sealing structure 590 seals the inner tube 120 at a side of the light source 130. The sealing structure 570 and the sealing structure 580 may fix the distance between the outer tube 110 and the inner tube 120.

FIG. 6 is a schematic diagram of a design of the illumination apparatus according to an embodiment of the disclosure. For clarity, only some of the components are shown in FIG. 6, and the thicknesses of the outer tube 110 and the inner tube 120 are omitted. Referring to FIG. 6, it is assumed that the radius of the inner tube 120 of the illumination apparatus 600 of this embodiment is r1, the radius of the outer tube 110 is r2, a tube radius difference between the outer tube 110 and the inner tube 120 is D, a length of the refractive structure 350 is H, a distance between the refractive structure 350 and the inner tube 120 at the light exit O is a, and a length of the segment 120a that protrudes from the light exit O is b. In an embodiment, the following relationship is satisfied: $0.5 \leq H/D \leq 2$, $0.04 \leq a/D \leq 0.33$, $0 < b \leq 7a + 0.1D$, and $b \leq H$, wherein $D = r2 - r1$. Nevertheless, the disclosure is not limited thereto.

Figure 7A:
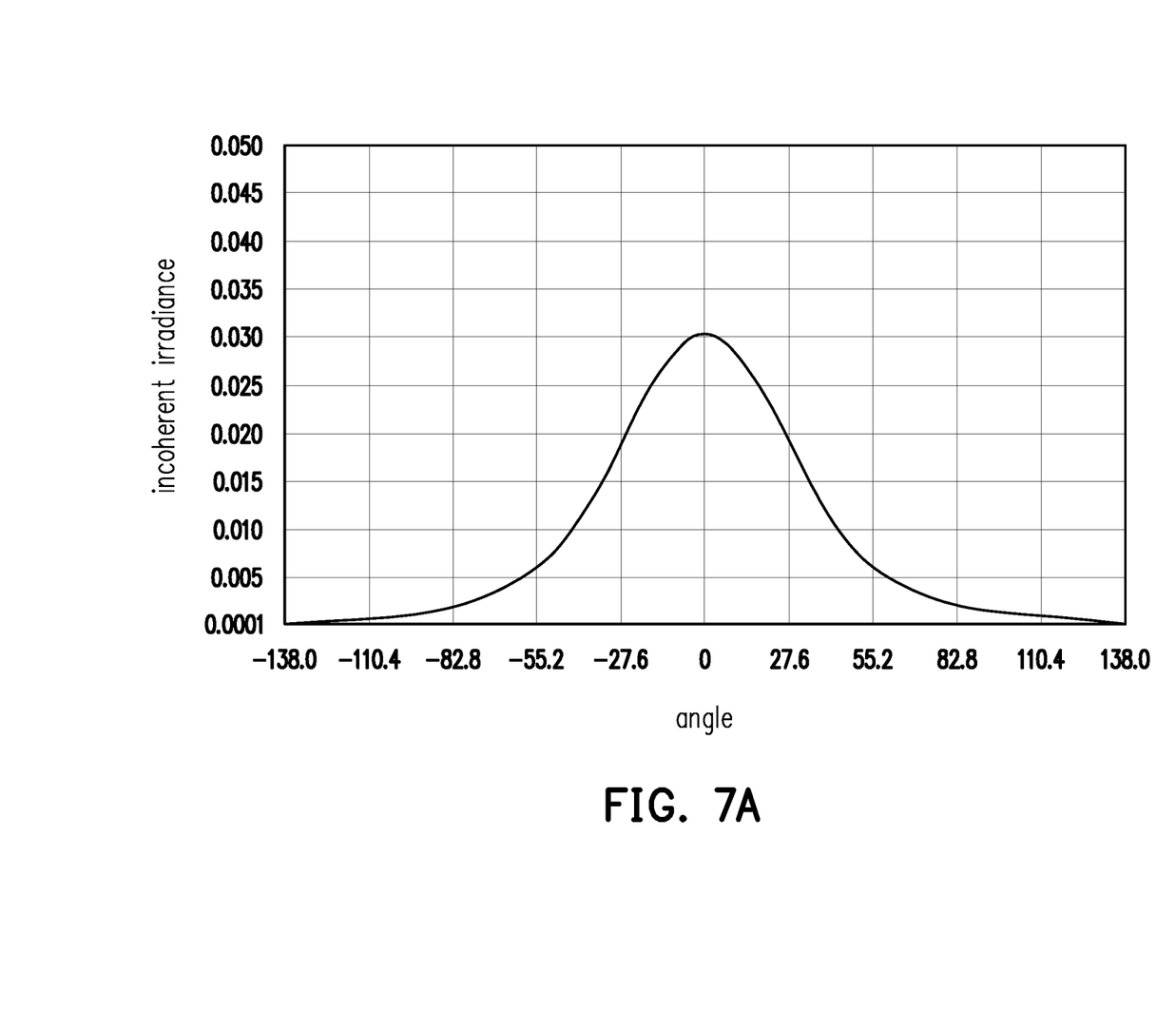
FIG. 7A is an incoherent irradiance distribution diagram in the case where a light-emitting diode is used as the illumination apparatus.
Figure 7B:
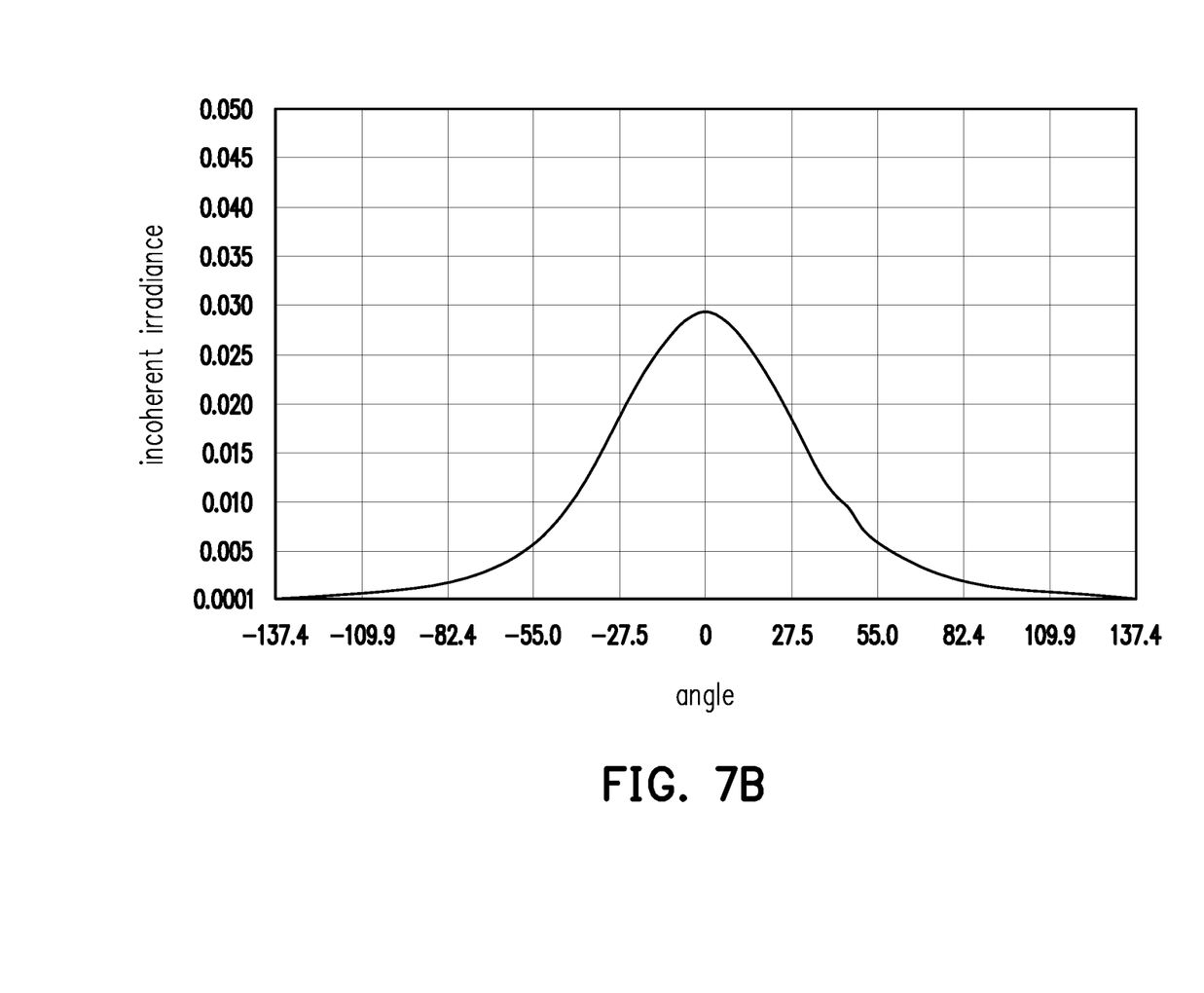
FIG. 7B is an incoherent irradiance distribution diagram in the case where a light-emitting diode and a secondary optical lens are used as the illumination apparatus.
Figure 7C:
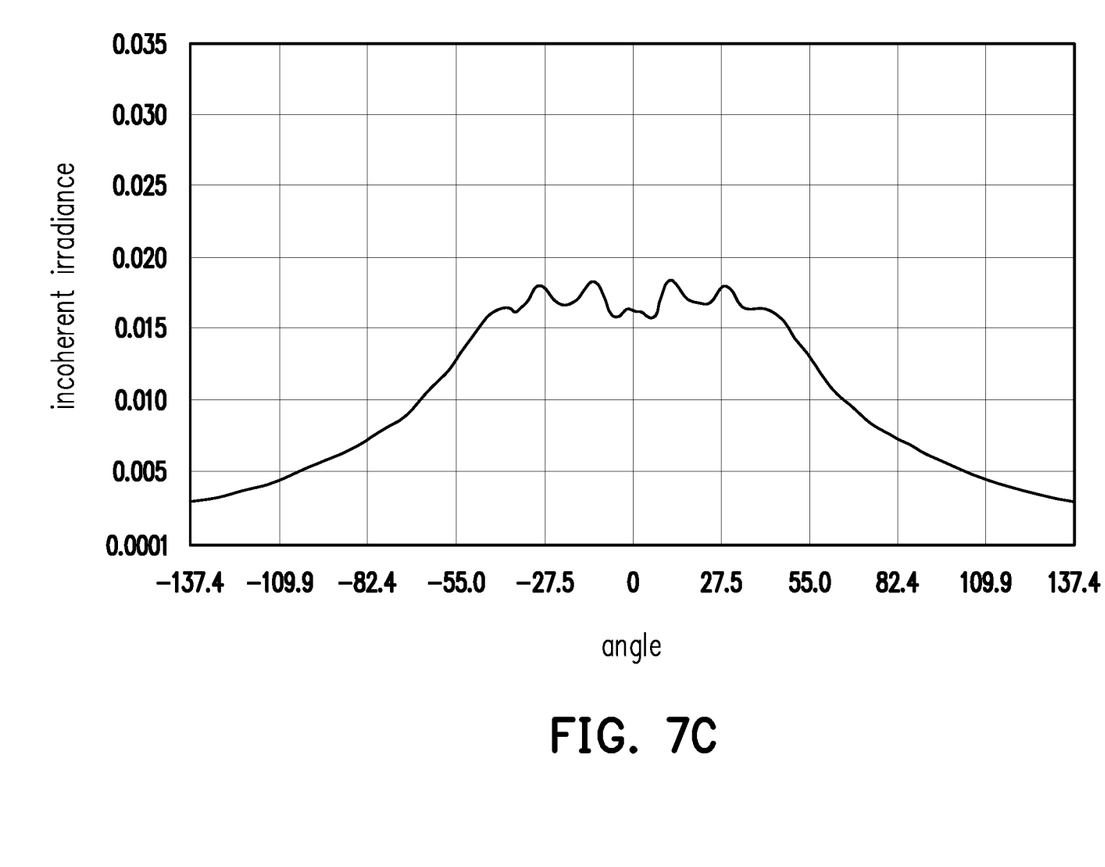
FIG. 7C is an incoherent irradiance distribution diagram of the illumination apparatus 300 according to an embodiment of the disclosure.

FIG. 7A is an incoherent irradiance distribution diagram in the case where a light-emitting diode is used as the illumination apparatus. FIG. 7B is an incoherent irradiance distribution diagram in the case where a light-emitting diode and a secondary optical lens are used as the illumination apparatus. FIG. 7C is an incoherent irradiance distribution diagram of the illumination apparatus 300 according to an embodiment of the disclosure. Referring to FIG. 7A, FIG. 7B, and FIG. 7C, it is known from the incoherent irradiance distribution diagrams that the irradiance distribution of the illumination apparatus 300 of the embodiment of the disclosure is more uniform than the case where only a light-emitting diode is used as the illumination apparatus and the case where only a light-emitting diode and a secondary optical lens are used as the illumination apparatus. When the central luminance of the region right in front of the illumination apparatus is 100%, in the illumination region of the illumination apparatus using only a light-emitting diode (as shown in FIG. 7A), the viewing angle at where the luminance is 80% of the central luminance is 39.6 degrees and the field of view (FOV) of the illumination apparatus is 56.6 degrees; in the illumination region of the illumination apparatus using a light-emitting diode and a secondary optical lens (as shown in FIG. 7B), the viewing angle at where the luminance is 80% of the central luminance is 42.2 degrees and the field of view (FOV) of the illumination apparatus is 60.3 degrees; and in the illumination region of the illumination apparatus 300 according to the embodiment of the disclosure, the viewing angle at where the luminance is 80% of the central luminance is 93.8 degrees and the field of view (FOV) of the illumination apparatus 300 (as shown in FIG. 7C) is 134 degrees. In other words, the illumination apparatus 300 according to the embodiment of the disclosure has a uniform luminance and is applicable to an illumination range of a large field of view.

It should be noted that, according to the detection method of the international standard ISO 8600: the luminance uniformity is calculated by obtaining the central luminance of the region right in front of the light-emitting device; obtaining the luminance at where the angle is 70% of the angle of the field of view; and dividing the luminance at where the angle is 70% of the angle of the field of view by the central luminance of the region right in front. Since the luminance uniformity in the embodiment of the disclosure is 80%, the angle of the field of view (FOV), as mentioned above, is calculated by: setting the central luminance of the region right in front of the light-emitting device as 100%; finding the region where the luminance is 80% of the central luminance and defining the viewing angle with respect to the central axis at where the luminance is 80% of the central luminance as 70% of the angle of the field of view; and then dividing this viewing angle by 70% to obtain the angle of the field of view.

Referring to FIG. 2, FIG. 3, and FIG. 7C, in the illumination region of the illumination apparatus 200 according to the embodiment of FIG. 2, the viewing angle at where the luminance is 80% of the central luminance is 69.4 degrees and the field of view of the illumination apparatus 200 is 99.1 degrees. In the illumination region of the illumination apparatus 300 according to the embodiment of FIG. 3, the viewing angle at where the luminance is 80% of the central luminance is 93.8 degrees and the field of view of the illumination apparatus 300 is 134 degrees. It is known from the above that the refractive structure and the light diffusion structure further improve the uniformity of the illumination apparatus.

To sum up, in the illumination apparatus according to the embodiments of the disclosure, a segment of the inner tube protrudes from the light exit. After the light emitted from the light source is reflected multiple times by the reflecting inner wall of the outer tube and the reflecting outer wall of the inner tube, more light beams are emitted from the illumination apparatus in the direction away from the inner tube. Therefore, the light beam has a larger divergence angle when leaving the illumination apparatus, so as to improve the luminance of the region at a larger viewing angle and prevent the light beam from being overly concentrated on the region right in front of the illumination apparatus. As a result, the illumination apparatus of the embodiments of the disclosure has a uniform luminance. Furthermore, the light diffusion structure according to the embodiments of the disclosure diverges the light that passes through, such that the light beam emitted from the light source is further dispersed and becomes uniform after passing through the light diffusion structure. In addition, after passing through the refractive structure, the light beam emitted from the light source is refracted by the refractive structure or totally internally reflected in the refractive structure to travel out of the illumination apparatus in the direction further away from the central axis. Therefore, the illumination apparatus according to the embodiments of the disclosure has a more uniform luminance.

It will be apparent to those skilled in the art that various modifications and variations can be made to the structure of the disclosed embodiments without departing from the scope or spirit of the disclosure. In view of the foregoing, it is intended that the disclosure covers modifications and variations of this disclosure provided they fall within the scope of the following claims and their equivalents.

What is claimed is:

1. An illumination apparatus, comprising:
an outer tube having a reflecting inner wall;
an inner tube disposed in the outer tube and coaxial with the outer tube, wherein the inner tube has a reflecting outer wall, a ring-shaped light channel is formed between the outer tube and the inner tube, the ring-shaped light channel has a light entrance and a light exit corresponding to two ends of the outer tube respectively, and a segment of the inner tube protrudes from the light exit; and a light source disposed at the light entrance, wherein a light beam emitted from the light source enters the ring-shaped light channel through the light entrance, is reflected multiple times by the reflecting inner wall of the outer tube and the reflecting outer wall of the inner tube, and then travels out of the illumination apparatus through the light exit.

2. The illumination apparatus according to claim 1, wherein a material of the outer tube and the inner tube comprises a metal.

3. The illumination apparatus according to claim 1, wherein the light source comprises a light-guiding optical fiber bundle or a light guide.

4. The illumination apparatus according to claim 1, wherein the light source comprises at least one light-emitting diode.

5. The illumination apparatus according to claim 1, further comprising a light diffusion structure disposed in the ring-shaped light channel.

6. The illumination apparatus according to claim 5, wherein the light diffusion structure comprises a transparent material and has a rough surface.

7. The illumination apparatus according to claim 5, wherein the light diffusion structure comprises a scattering material dispersed in the light diffusion structure.

8. The illumination apparatus according to claim 5, wherein the light diffusion structure comprises a holographic diffuser.

9. The illumination apparatus according to claim 1, further comprising a refractive structure disposed at the light exit of the ring-shaped light channel and connected to the outer tube, wherein the light beam travels out of the illumination apparatus in a direction away from the inner tube through the refractive structure.

10. The illumination apparatus according to claim 9, wherein an outer diameter of the refractive structure is equal to an outer diameter of the outer tube, and an inner diameter of the refractive structure at a junction with the outer tube is smaller than an inner diameter of the refractive structure at an end away from the outer tube.

11. The illumination apparatus according to claim 9, wherein an inner diameter of the refractive structure at a junction with the outer tube is greater than an outer diameter of the inner tube.

12. The illumination apparatus according to claim 9, wherein an inner diameter of the refractive structure at an end away from the outer tube is smaller than or equal to an outer diameter of the outer tube.

13. The illumination apparatus according to claim 9, wherein when a radius of the inner tube is r1, a radius of the outer tube is r2, a tube radius difference between the outer tube and the inner tube is D, and a length of the refractive structure is H, $0.5 \leq H/D \leq 2$, wherein $D=r2-r1$.

14. The illumination apparatus according to claim 9, wherein when a radius of the inner tube is r1, a radius of the outer tube is r2, a tube radius difference between the outer tube and the inner tube is D, and a distance between the refractive structure and the inner tube at the light exit is a, $0.04 \leq a/D \leq 0.33$, wherein $D=r2-r1$.

15. The illumination apparatus according to claim 9, wherein when a radius of the inner tube is r1, a radius of the outer tube is r2, a tube radius difference between the outer tube and the inner tube is D, a length of the refractive structure is H, a distance between the refractive structure and the inner tube at the light exit is a, and a length of the segment that protrudes from the light exit is b, $0<b \leq 7a+0.1D$ and $b \leq H$, wherein $D=r2-r1$.

16. The illumination apparatus according to claim 9, further comprising a light diffusion structure disposed in the ring-shaped light channel.

17. The illumination apparatus according to claim 16, wherein the light diffusion structure comprises a transparent material and has a rough surface.

18. The illumination apparatus according to claim 16, wherein the light diffusion structure comprises a scattering material dispersed in the light diffusion structure.

19. The illumination apparatus according to claim 16, wherein the light diffusion structure comprises a holographic diffuser.

20. The illumination apparatus according to claim 16, wherein the light diffusion structure is disposed on the refractive structure and close to the light exit of the ring-shaped light channel.

21. The illumination apparatus according to claim 16, wherein the light diffusion structure and the refractive structure are integrally formed.

22. The illumination apparatus according to claim 1, further comprising an image capturing device disposed in the inner tube at an end close to the segment.

* * * * *